United States Patent [19]
Kinicki et al.

[11] Patent Number: 5,315,999
[45] Date of Patent: May 31, 1994

[54] ULTRASOUND IMAGING SYSTEM HAVING USER PRESET MODES

[75] Inventors: Rachel M. Kinicki, Acton; Kerry Short, Bradford, both of Mass.; Joseph Kobrenski, Salem, N.H.; Janice Bisson, Methuen, Mass.

[73] Assignee: Hewlett-Packard Company, Palo Alto, Calif.

[21] Appl. No.: 50,951

[22] Filed: Apr. 21, 1993

[51] Int. Cl.⁵ ............................................. A61B 8/00
[52] U.S. Cl. ......................... 128/660.07; 364/413.25
[58] Field of Search .................... 128/660.04, 660.07, 128/660.01, 661.03; 73/626; 358/461; 3643/413.14, 413.16, 413.25

[56] References Cited

U.S. PATENT DOCUMENTS

| | | | |
|---|---|---|---|
| 4,099,419 | 7/1978 | Kuroda et al. | 73/626 |
| 4,578,767 | 3/1986 | Shapiro | 364/550 |
| 4,751,570 | 6/1988 | Robinson | 358/88 |
| 4,792,910 | 12/1988 | Lange | 364/519 |
| 4,836,026 | 6/1989 | P'an et al. | 73/620 |
| 4,847,765 | 7/1989 | Nonnweiler et al. | 364/413.13 |
| 4,896,278 | 1/1990 | Grove | 364/552 |
| 5,058,591 | 10/1991 | Companion et al. | 128/661.03 |
| 5,072,735 | 12/1991 | Okazaki et al. | 128/660.07 |
| 5,113,706 | 5/1992 | Pittaro | 73/626 |
| 5,157,518 | 10/1992 | Ohtaki et al. | 358/461 |
| 5,161,535 | 11/1992 | Short et al. | 128/660.01 |
| 5,211,167 | 5/1993 | Amenomri | 128/660.04 |

*Primary Examiner*—William E. Kamm
*Assistant Examiner*—George Manuel

[57] ABSTRACT

In an ultrasound imaging system, sets of imaging parameter values are saved as preset modes. When a user later selects one of the preset modes, the system automatically operates in accordance with the corresponding set of imaging parameter values. The imaging parameter values for each preset mode are selected and adjusted by the user while the system is generating a desired ultrasound image, thereby ensuring that the stored imaging parameter values correspond to a desired ultrasound image. The system can store preset modes for different exam types, for different image displays, for different patients and for different users. Each of the preset modes can be selected with a single keystroke.

18 Claims, 7 Drawing Sheets

ULTRASOUND IMAGING SYSTEM HAVING USER PRESET MODES

FIELD OF THE INVENTION

This invention relates to ultrasound imaging systems and, more particularly, to ultrasound imaging systems wherein imaging modes can be preset by a user for subsequent use. Each imaging mode can be preset while a desired ultrasound image is being displayed by the system.

BACKGROUND OF THE INVENTION

Ultrasound imaging is widely used in medical applications to noninvasively observe structures within the human body, such as cardiac structures, the vascular system, the fetus, the uterus, the abdominal organs and the eye. In a typical imaging system, short bursts of ultrasound energy are directed into a patient's body with a handheld transducer. The returning reflected energy, or echos, are received by the same transducer. The signals representing the reflected energy are processed and formatted into a video image of the target region.

The ultrasound imaging system has a number of imaging parameters that control transmission and reception of ultrasound energy, processing of received signals and image display. Different organs and regions of the human body may require very different imaging parameters due to the different depths, sizes and tissue types of the structures being imaged. Furthermore, the ultrasound imaging system typically has several display modes for presenting different images of a target region. Examples include two-dimensional imaging, M-mode imaging, color flow imaging and Doppler imaging. For each of these display modes, various imaging parameters are adjustable. In order for an ultrasound imaging system to provide flexibility, many imaging parameters must be adjustable. Thus, adjustment of a number of imaging parameters is required to obtain a desired ultrasound image. If the imaging parameters were manually adjusted each time the instrument were used to obtain a different image, a high degree of user skill would be required. Furthermore, the manual adjustment procedure would be time consuming.

A further difficulty is that the ultrasound imaging system is typically located in a hospital where different users may operate the system at different times. Thus, a user may find the imaging system in an unknown state as a result of operation by a different user.

The problem has been partially alleviated in prior art systems by providing predetermined operating modes, such as cardiac, vascular and obstetrics. However, within each predetermined operating mode, many imaging parameters are adjustable. Thus, while use of the imaging system is simplified to some extent, adjustment for a particular exam can still be difficult and time consuming.

A further difficulty with prior art systems relates to the frequent need to perform repetitive tests. In order to obtain consistent and reliable results, the imaging system should have the same parameter settings for each test of the same type. With prior art systems, it has been difficult or impossible to return to a previous set of imaging parameters after the system has been used for a different test. The predetermined operating modes described above are insufficient for two reasons. To cover all possible imaging parameter settings would require an unacceptably large number of predetermined operating modes, many of which would be unused in any particular hospital. Second, users typically adjust imaging parameters after selection of a predetermined operating mode in order to optimize the ultrasound image.

Prior art systems typically utilize control knobs or switches wherein each parameter value is determined by the mechanical position of a control switch or adjustment knob. Storage of these values for later use is not feasible, because the stored parameter values would differ from the parameter values indicated by the control switches and adjustment knobs, and thereby cause user confusion. Several prior art systems permit storage of several parameter values for later use. However, these parameter values must be selected or typed into the system at a time when the user is unable to observe the desired ultrasound image.

A medical ultrasound imaging system which utilizes an electroluminescent touch panel is disclosed in U.S. Pat. No. 5,161,535, issued Nov. 10, 1992 to Short et al.

SUMMARY OF THE INVENTION

According to a first aspect of the invention, an ultrasound imaging system comprises image generating means for generating an ultrasound image in accordance with preselected imaging parameters, means for storing a set of imaging parameter values selected by a user while the image generating means is generating a desired ultrasound image, the set of imaging parameter values defining a preset mode, and means responsive to subsequent user selection of the preset mode for automatically operating the image generating means in accordance with the stored set of imaging parameter values.

The user configures preset modes by adjusting the system in the same manner as is done for real time imaging. An image is observed while the imaging parameter values are being selected and adjusted, in contrast to prior art systems where the user was required to fill out a form with desired parameters or to select parameters from a list, and was unable to observe an image until after the parameters had been selected.

The ultrasound imaging system preferably further includes a touch panel for parameter display and selection, and one or more control devices for adjusting the values of the imaging parameters. The control devices are used to adjust the stored imaging parameter values. The imaging parameter values are determined by the stored values rather than the mechanical positions of the control devices. The stored set of imaging parameter values is supplied to the touch panel in response to user selection of the preset mode.

Preferably, the ultrasound imaging system stores a plurality of sets of imaging parameter values, each set corresponding to a preset mode. In response to user selection of a preset mode, the image generating means is automatically operated with the corresponding set of imaging parameter values.

According to another aspect of the invention, a method for operating an ultrasound imaging system is provided. The system includes image generating means for generating an ultrasound image in accordance with preselected imaging parameters. The method of the invention comprises the steps of storing a set of imaging parameter values selected by a user while the image generating means is generating a desired ultrasound image, the set of parameter values defining a preset mode, and responding to subsequent user selection of the preset mode by automatically operating the image generating means in accordance with the stored set of imaging parameter values.

BRIEF DESCRIPTION OF THE DRAWINGS

For a better understanding of the present invention, reference is made to the accompanying drawings, which are incorporated herein by reference and in which.

DETAILED DESCRIPTION

The present invention provides methods and apparatus for operating an ultrasound imaging system wherein sets of imaging parameter values are saved as preset modes. When a user later selects one of the preset modes, the system automatically operates with the corresponding set of imaging parameter values. The imaging parameter values for each preset mode are selected and adjusted by the user while the system is generating a desired ultrasound image, thereby ensuring that the stored imaging parameter values correspond to a desired ultrasound image. The system can store a plurality of preset modes for different exam types, for different image displays, for different patients and for different users. Each of the preset modes can typically be selected with a single keystroke. As a result, each user of the system can easily return to his or her preferred imaging modes.

Figure 1:
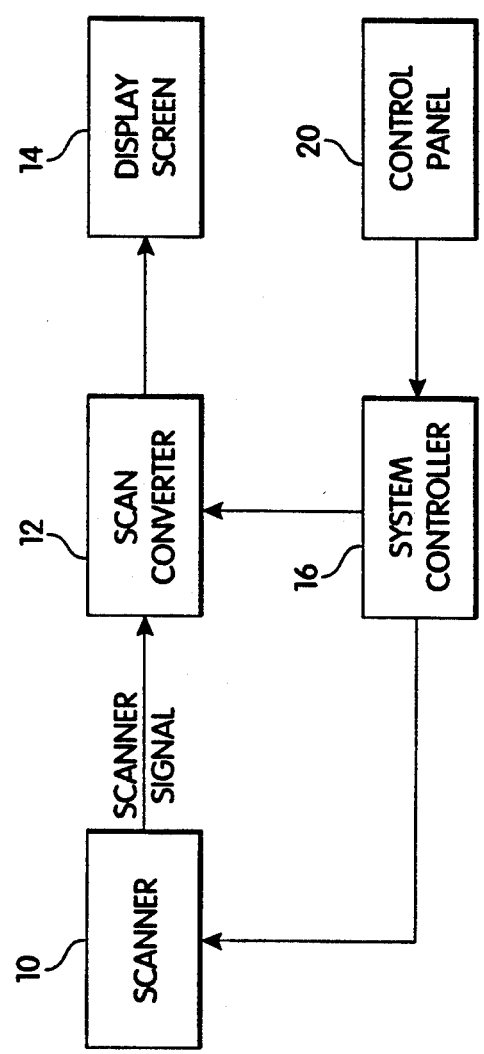
FIG. 1 is a block diagram of an ultrasound imaging system in accordance with a preferred embodiment of the invention.

A simplified block diagram of an ultrasound imaging system suitable for incorporation of the present invention is shown in FIG. 1. A scanner 10 performs ultrasound scanning of a specified region of a patient's body. The scanner 10 includes an ultrasound transducer for transmitting and receiving ultrasound energy. The transducer transmits ultrasound energy into a region being imaged and receives reflected ultrasound energy from various structures and organs within the patient's body.

The transducer may include an array of transducer elements. As is known in the prior art, by appropriately delaying the pulses applied to each transducer element, a focused ultrasound beam is transmitted along a desired scan line. Reflected ultrasound energy from a given point within the patient's body is received by the transducer elements at different times. The transducer elements convert the received ultrasound energy to electrical signals which are supplied to a receive beamformer. The delayed signals from each transducer element are summed by the beamformer to provide a scanner signal that is a representation of the reflected energy level along a given scan line. The process is repeated for multiple scan lines to provide signals for generating an image of the prescribed region of the patient's body. Typically, the scan pattern is a sector scan, wherein the scan lines originate at the center of the ultrasound transducer and are directed at different angles. A linear, curvilinear or any other scan pattern can also be utilized.

The scanner signal is applied to a scan converter 12, of a type known in the art, which converts the sector scan information generated by scanner 10 to a conventional master scan display signal. The output of scan converter 12 is applied to a video display screen 14, which displays an image of the desired region of the patient's body. A system controller 16 provides overall control of the system. The system controller 16 performs timing and control functions and may include a microprocessor, such as an Intel 68020, and associated memory. A control panel 20 permits user control of the system as described below.

Figure 2:
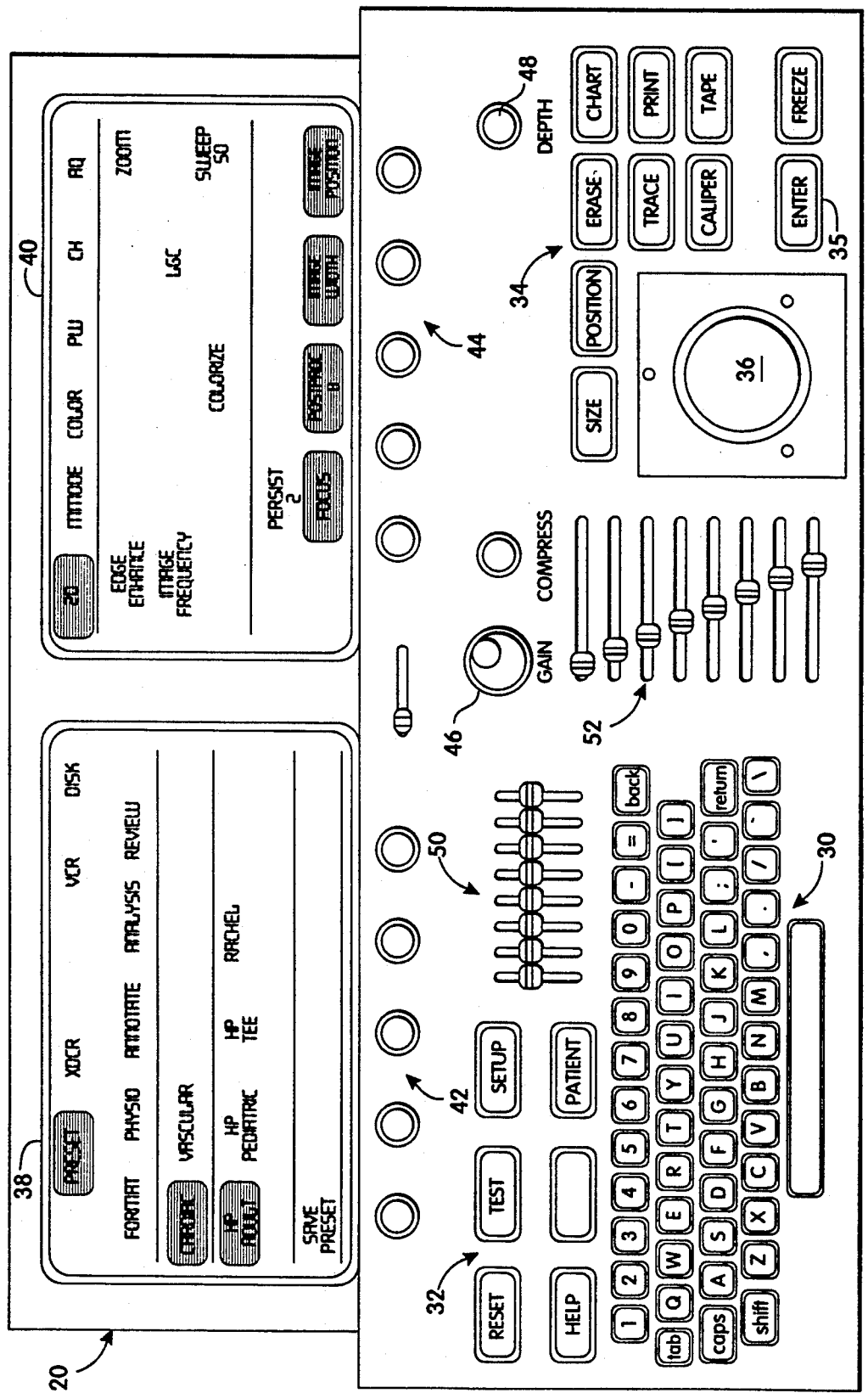
FIG. 2 shows a preferred embodiment of a control panel for the ultrasound imaging system of FIG. 1.

The control panel 20, in accordance with a preferred embodiment of the invention, is shown in FIG. 2. The control panel 20 includes a conventional alphanumeric keyboard 30, dedicated function keys 32 and 34, including Enter key 35, a trackball 36, touch panels 38 and 40, soft adjustment knobs 42a, 42b, 42c, 42d, 42e and 44a, 44b, 44c, 44d, 44e, gain control 46, depth control 48, lateral gain control (LGC) 50 and time gain control (TGC) 52. The keyboard 30 permits entry of the required alphanumeric information. The trackball 36 permits control of the position of a cursor on the display screen 14 in operating modes where a cursor is utilized.

Figure 3A:
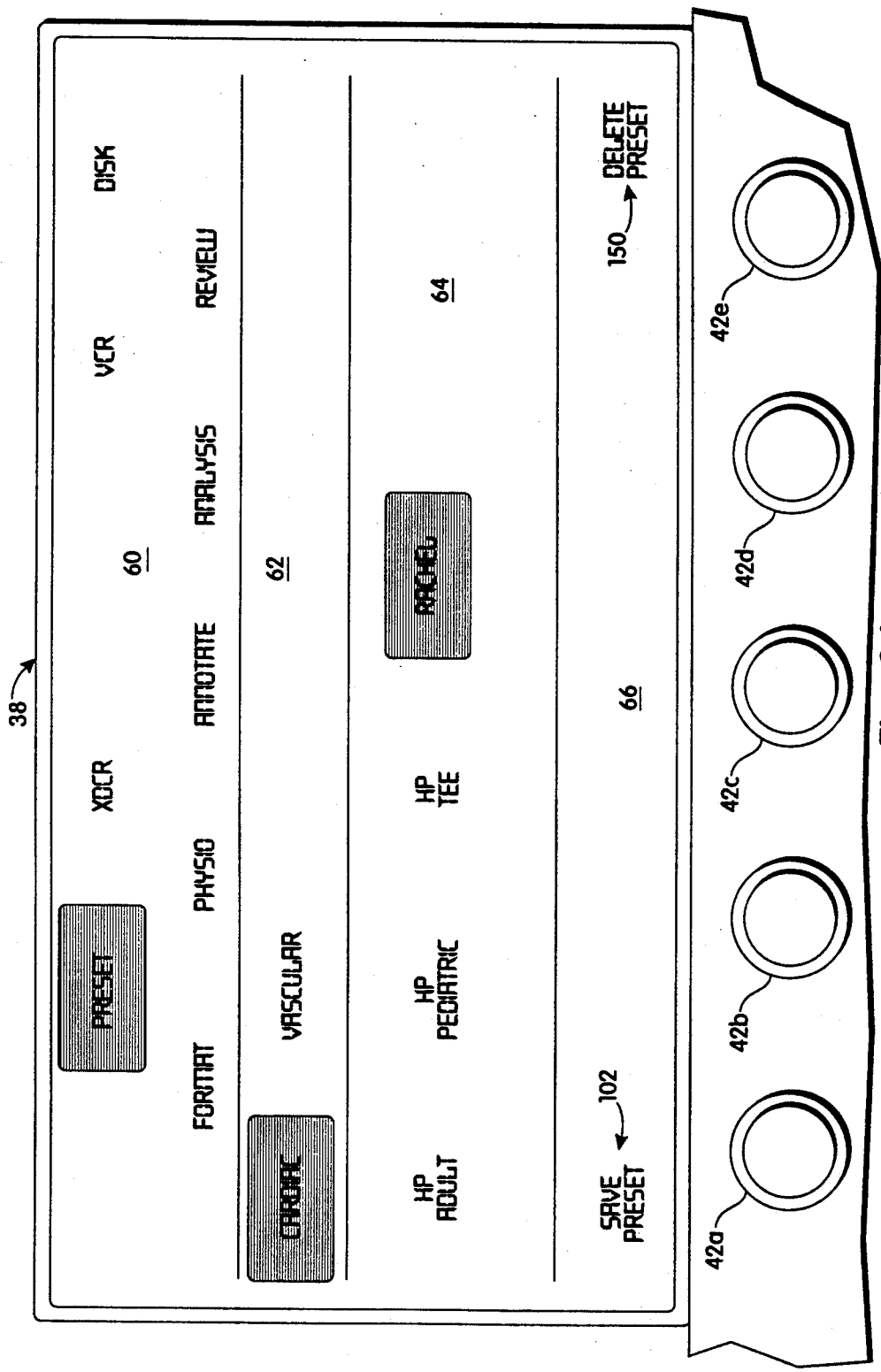
FIGS. 3A and 3B show touch panels used in the control panel of FIG. 2.
Figure 3B:
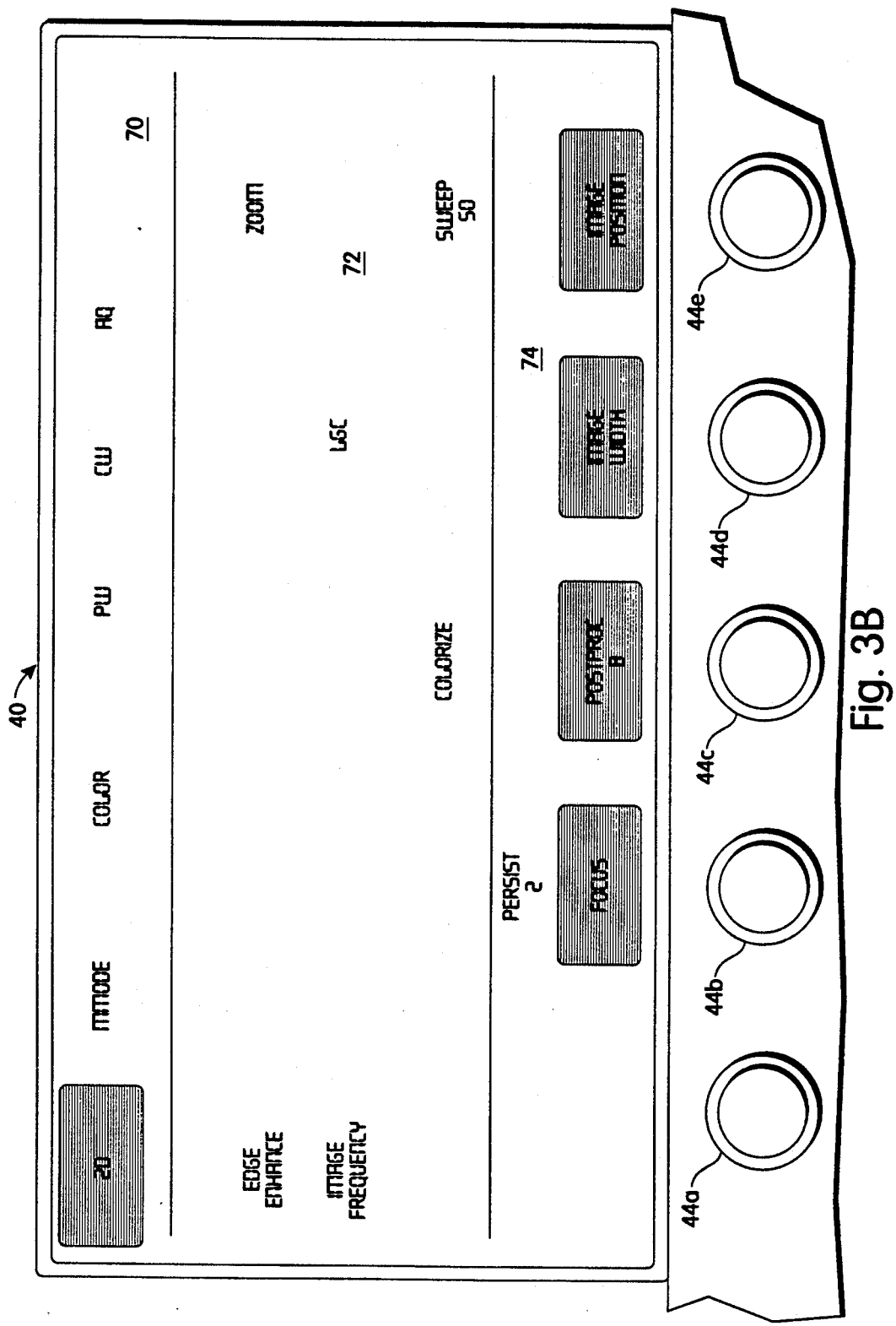

An enlarged view of the touch panel 38 and adjustment knobs 42a–42e is shown in FIG. 3A. An enlarged view of touch panel 40 and adjustment knobs 44a–44e is shown in FIG. 3B. These elements are used in conjunction with the other elements of the control panel 20 to control operation of the ultrasound imaging system. The touch panels 38 and 40 display information regarding the status of the system and permit user selection of various functions and parameters.

The touch panels include display keys, which may be inactive or active. Active display keys are relevant to the current operating mode of the system and are displayed on the touch panel. Inactive display keys are not relevant to the current operating mode of the system and do not appear on the touch panel. Active display keys may be selected or deselected. With reference to FIG. 3A, the Vascular key is an active but deselected display key; the Cardiac key is an active and selected display key. Active display keys are represented by a word or abbreviation that describes the function of the key. A selected display key has a highlighted display area, whereas a deselected display key is not highlighted. The user may select or deselect a display key by touching the panel in the display key area. It will be understood that different display keys appear on the touch panels 38 and 40 for different operating modes, under control of software in the system controller 16. In a preferred embodiment, the touch panels 38 and 40 are electroluminescent panels, such as analog resistive touch panels manufactured by Brady USA Thin Film Products, having 256 by 256 pixels.

The adjustment knobs 42a–42e and 44a–44e are typically attached to variable resistors or multiple position switches. As best shown in FIG. 3B, the adjustment knobs are preferably located directly below specified display keys in touch panels 38 and 40. Thus, for example, adjustment knob 44d is located below the Image Width display key, and adjustment knob 44e is located below the Image Position display key. In the imaging mode shown in FIG. 3B, adjustment knob 44d is used to vary the image width, and adjustment knob 44e is used to vary the image position in the ultrasound display. In some instances, one or more display keys in the bottom line of touch panels 38 and 40 are not associated with the adjustment knobs located below them.

The adjustment knobs 42a-42e and 44a-44e are so-called "soft adjustment knobs". This means that the value assigned to the imaging parameter which the knob controls is determined, not by the mechanical position of the knob, but by the value stored in the system controller 16. Thus, for example, the adjustment knob 44d can be used to increase or decrease the image width in the display mode shown. However, the image width parameter value is determined by the value stored in system controller 16 rather than by the mechanical position of adjustment knob 44d.

The adjustment knobs 42a-42e and 44a-44e may be used to vary different imaging parameters in different operating modes. Thus, for example, in a color display mode, a different display key may be located above adjustment knob 44d, and the adjustment knob 44d, is used to control that parameter. This configuration permits use of preset modes as described below, because each preset mode utilizes the parameter values stored in system controller 16. Since the adjustment knobs 42a-42e and 44a-44e have no panel labels, and specific values are not associated with the positions of the knobs, the parameter values stored in the system controller 16 can be utilized without user confusion.

In a preferred embodiment, the touch panels 38 and 40 are organized as follows. Each selection on the touch panel is represented by a display key which includes a function or parameter name. As shown in FIG. 3A, a region 60 of touch panel 38 includes display keys for user selection of various system functions, such as Preset, Format, and Analysis display keys. The preset mode is the only mode that is relevant to the present invention and is indicated in FIG. 3A as being selected. When the preset function is selected, a region 62 of touch panel 38 includes display keys for user selection of exam type. In a preferred embodiment, cardiac, vascular and obstetric exam types are available. When the preset function is selected, a region 64 of touch panel 38 includes display keys for user selection of various preset modes within the selected exam type. When the preset function is selected, a region 66 of touch panel 38 includes a Save Preset key 102. When the currently active preset mode is a user preset mode, the region 66 includes a Delete Preset key 150. The use of the Save preset key 102 and the Delete Preset key 150 is described below.

In a preferred embodiment, the preset modes include one or more factory preset modes, such as adult and pediatric in FIG. 3A, which cannot be modified by the user. The preset modes may also include one or more user presets as described in detail below. Each preset mode has a corresponding set of imaging parameter values, which are stored by the system controller 16. When one of the preset modes is selected, the system controller 16 automatically operates the system in accordance with the stored set of imaging parameter values that corresponds to the selected preset mode. When a preset mode is selected, that preset mode becomes the current active mode of the system. The corresponding set of imaging parameter values is read from memory in system controller 16, is displayed on touch panels 38 and 40 and is used to control the operation of the system. Some imaging parameter values may not be included in presets, since these values are normally adjusted during every exam based on the patient and the clinical need. These parameters can be set to fixed default values whenever a preset mode is selected.

Referring now to FIG. 3B, touch panel 40 in the preferred embodiment includes a region 70 having display keys for user selection of an image display mode, such as Two-dimensional, M mode, and Color display keys. The display panel 40 further includes a region 72 having display keys which indicate the imaging parameters that are relevant to the selected display type. A region 74 of touch panel 40 includes display keys for parameters that can be varied by adjustment knobs 44a-44e. Within each preset mode, the imaging parameters can be adjusted by the user to obtain an optimum image. Region 72 is typically used for on/off functions, and region 74 is typically used for multiple value functions. The multiple value functions may have discrete or continuous values. The preset modes permit a user to return to a desired set of imaging parameter values using a single keystroke. In most cases, the manual adjustment of imaging parameters required to obtain an optimum image in a preset mode is minimal.

The preset modes described herein are frequently used for creating preset imaging modes. However, it will be understood that the preset modes described herein can be used in connection with any operating mode of the system. For example, preset modes can be used in connection with annotation and analysis modes of the ultrasound imaging system.

The creation, modification and deletion of preset modes is described in detail below. These functions are preferably controlled by a software program in the system controller 16. In a preferred embodiment, the program is implemented in the C programming language.

Figure 4A:
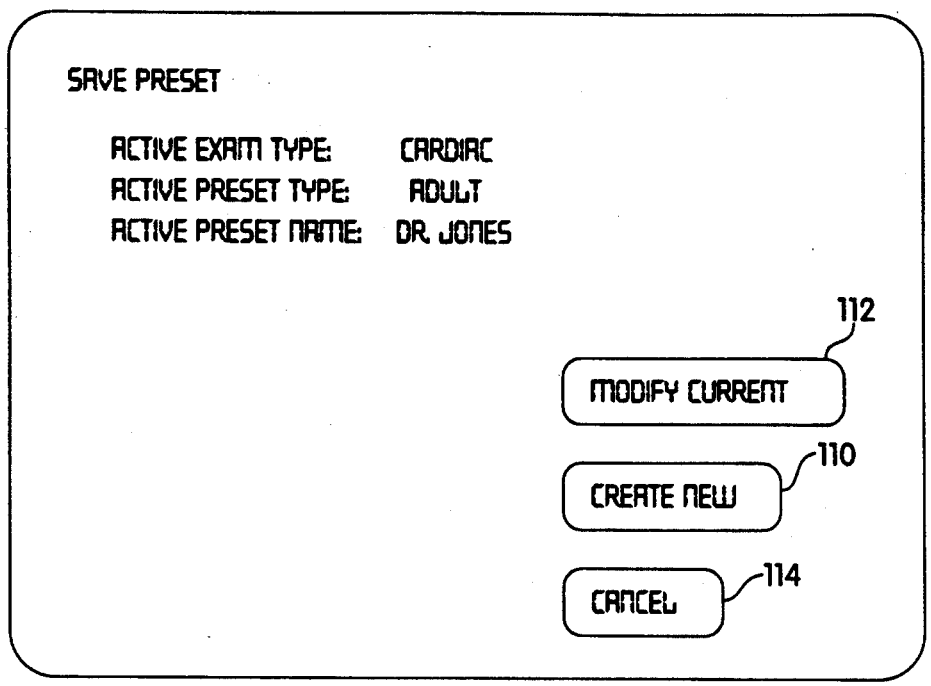
FIGS. 4A to 4D show dialog boxes used in connection with the preset function of the present invention.
Figure 4B:
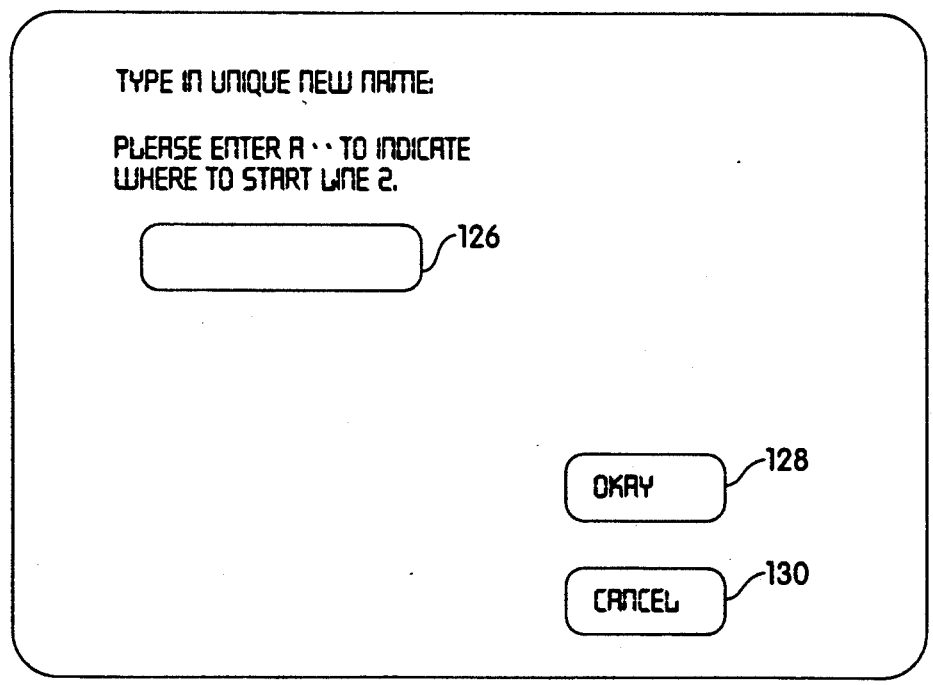
Figure 5:
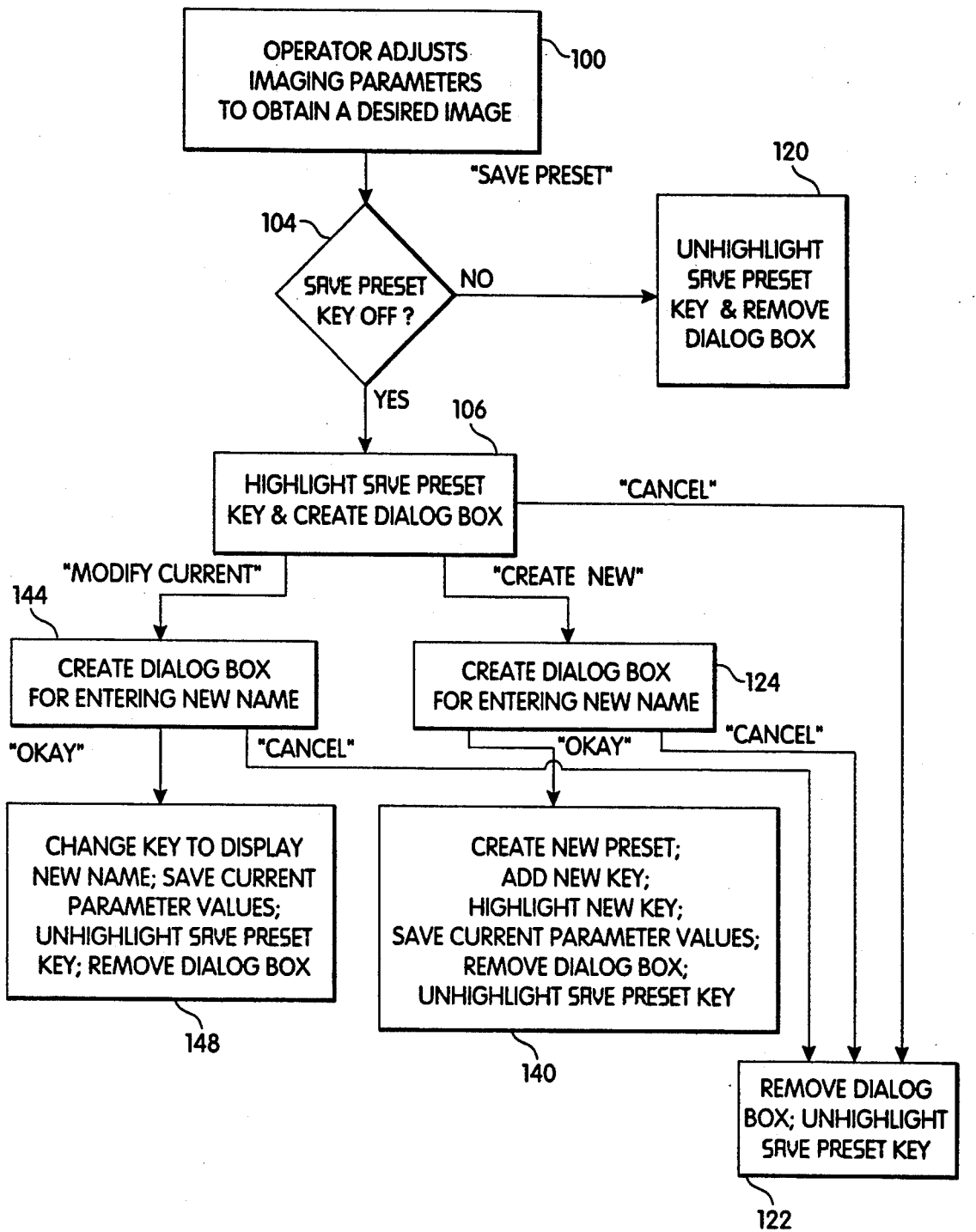
FIG. 5 is a flow diagram of the preset function of the present invention.

A flow chart of the process for creating new preset modes and for modifying existing preset modes is shown in FIG. 5. Dialog boxes which appear on the display screen 14 during this process are illustrated in FIGS. 4A and 4B. Initially, the operator selects an exam type and preset mode and adjusts the imaging parameter values to obtain a desired image on the display screen 14 (step 100). The adjustment of imaging parameter values is typically done by selecting an existing preset mode, either a factory preset mode or a previously established user preset mode, that is closest to the desired exam type and the desired image. The imaging parameters of the system are then adjusted using the control panel 20 to obtain a desired image. The image is preferably obtained by scanning an average patient. It is then expected that the preset mode can be used to obtain similar images when scanning other patients with the same imaging parameter values or with slightly adjusted imaging parameter values. Alternatively, the imaging parameters can be adjusted to desired values without scanning a patient.

When the user has adjusted the system to obtain a desired ultrasound image, the user selects the Save Preset key 102 (FIG. 3A) on touch panel 38. A new or modified preset mode is constructed from the currently active preset mode. In general, if the currently active preset mode is a factory preset mode and the maximum allowable number of user preset modes is not exceeded by the creation of a new preset mode, then the current system state can be used to create a new preset mode. The factory preset mode cannot be modified. If the currently active preset mode is a user preset mode and the maximum number of allowable preset modes is not exceeded by the creation of a new preset mode, then the current system state can be used to create a new preset mode or to modify the currently active user preset mode. When the maximum number of user preset modes has been reached, the current system state can be used to modify the currently active preset mode.

Referring again to FIG. 5, when the user selects the Save Preset display key, the system controller 16 determines if the Save Preset key was previously off, or deselected, in step 104. When the Save Preset key was off, it is highlighted in step 106 to indicate that the Save Preset function has been selected. In addition, a dialog box is created on the display screen 14. A dialog box for the case where the active preset mode is a user preset mode is shown in FIG. 4A. The dialog box includes a title to indicate the Save Preset function, the active exam type, the active preset type and the active preset name. If the active preset mode is a factory preset mode, then a warning (not shown) is printed in the dialog box to indicate that the factory preset mode cannot be modified. If the maximum number of preset modes has been reached, a warning message (not shown) is printed in the dialog box. If a display key is not available for a new preset mode, then a warning message (not shown) is printed in the dialog box. Otherwise, a Create New selection 110 is printed in the dialog box. When the active preset mode is a user preset mode, a Modify Current selection 112 is printed in the dialog box. When the active preset mode is a factory preset mode, the Modify Current selection 112 is not printed in the dialog box. Finally, a Cancel selection 114 is printed on the dialog box.

In step 104, when the Save Preset display key was previously on, or selected, and is touched by the user, the Save Preset key is unhighlighted in step 120 and any dialog box on the display screen 14 is removed.

From the dialog box shown in FIG. 4A, the user can select Create New, Cancel, or Modify Current (when the currently active preset mode is a user preset mode). The selection of one of the options in the dialog box of FIG. 4A is made by positioning the cursor on the desired selection using trackball 36 (FIG. 2) and pressing the Enter key 35. When the user selects Cancel, the system controller 16 removes the dialog box in step 122 (FIG. 5) and unhighlights the Save Preset key.

When the user selects Create New in the dialog box of FIG. 4A, the system controller 16 in step 124 generates a new dialog box as shown in FIG. 4B for entering a new preset name. The dialog box includes a title to indicate the Enter Preset Name function and a field 126 for entering the name of the preset mode. The dialog box also includes an Okay selection 128 and a Cancel selection 130. When the user enters a name in field 126 using keyboard 30 and selects Okay, the system controller 16 in step 140 first checks the name to be sure that it is not the same as an already existing name. Assignment of the same name to two preset modes is not permitted. If the name is unique, the system controller 16 creates a new preset mode. This operation includes saving the new name and saving the current system imaging parameter values, as well as annotation and analysis values. In addition, a new display key is added on the touch panel 38, and the new preset mode is made the active preset mode. The display key for the new preset mode is highlighted, and the dialog box is removed from the display screen 14. Finally, the Save Preset key is unhighlighted.

When in the dialog box shown in FIG. 4B for entering the preset name, the operator selects Cancel, the system controller 16 in step 122 removes the dialog box and unhighlights the Save Preset key.

When the user selects Modify Current in the dialog box of FIG. 4A, the system controller in step 144 creates a dialog box similar to the one shown in FIG. 4B for entering a new name. If the user enters a name in field 126 and selects Okay, the system controller 16 in step 148 saves the new name and changes the display key of the currently active preset mode to display the new name. The current system imaging parameter values are saved as the modified values of the currently active preset mode. The dialog box is removed from the display screen 14 and the Save Preset display key is unhighlighted.

When the user selects Cancel in the dialog box of FIG. 4A, the dialog box is removed from the display screen 14 and the Save Preset key is unhighlighted in step 122.

Figure 4C:
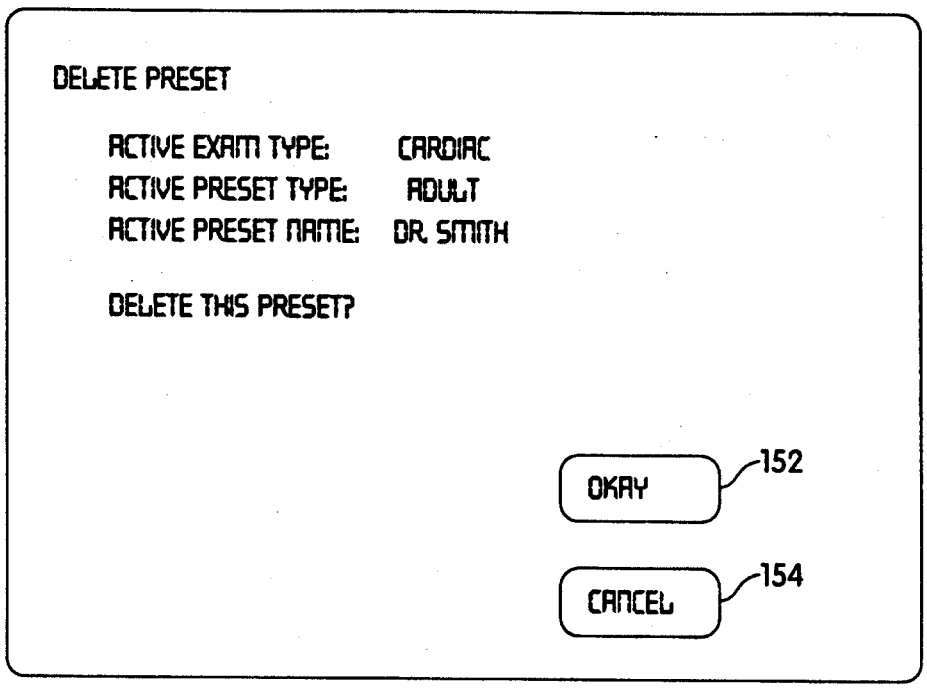

As shown in FIG. 3A, the touch panel 38 includes a Delete Preset key 150. Since only user preset modes can be deleted, the Delete Preset key is shown on touch panel 38 only when a user preset mode is the active preset mode. When a factory preset mode is the active preset mode, the Delete Preset key 150 is not shown on touch panel 38. When the user selects Delete Preset, a dialog box as shown in FIG. 4C is created on display screen 14. The dialog box includes a title to indicate the Delete Preset function, the active exam type, the active preset type and the active preset name. The dialog box further includes an Okay selection 152 and a Cancel selection 154. When the user selects Okay, the active preset mode is deleted from the system and the corresponding preset display key is deleted from touch panel 38. The active preset mode changes from the cancelled one to another one of those preset modes currently available for the same exam type, such as the first preset mode displayed at the left of the touch panel. When the user selects Cancel, the dialog box is removed from the display screen 14 and the Delete Preset key is unhighlighted. The active preset mode remains active.

Figure 4D:
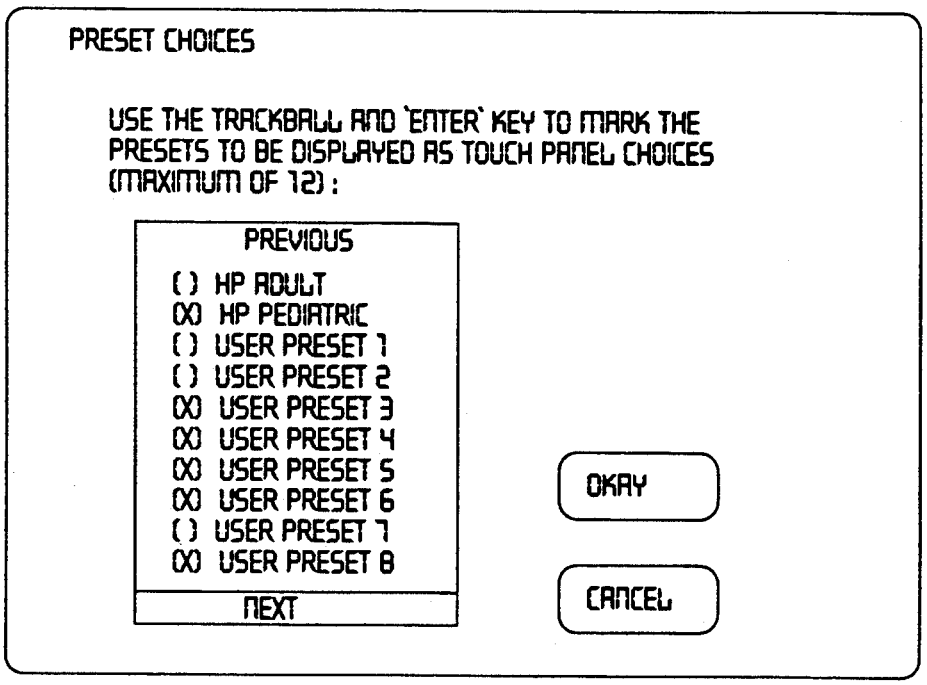

In a preferred embodiment, the touch panel 38 can accommodate a total of 12 preset modes for each exam type. A Preset Choices key (not shown) is available on the touch panel 38 in a preset setup control mode. The Preset Choices key is used to select which presets are to appear on the touch panel 38 and which are hidden from the user. When the user selects the Preset Choices key, a dialog box as shown in FIG. 4D is created on the display screen 14. The presets for the active exam type are displayed with a check box next to each preset name. Those presets that currently appear on the touch panel are marked with an "X" in the check box. The user can select and deselect presets that are to appear on the touch panel 38 using the trackball 36 and the Enter key. To complete the Preset Choices operation, either Okay or Cancel is selected.

The present invention has been shown and described above in connection with a phased array sector scan ultrasound system. It will be understood that the present invention is not limited to any particular type of ultrasound system. Thus, the invention can be used with phased array or mechanical scanners, with linear or curvilinear transducers and with any scan format. Furthermore, the invention is not limited to use with a touch panel as shown and described. The primary requirement is that the user control panel employ soft control keys and adjustment devices so that the system is operated in accordance with stored sets of imaging parameter values. This avoids the confusion that may occur when the currently active imaging parameters are not the same as those indicated by the positions of the control knobs and switches.

In accordance with the present invention, a preset mode is obtained with a single keystroke on the touch panel. The ultrasound imaging system is automatically initialized to the stored set of imaging parameter values that correspond to the preset mode. The number of user adjustments required to achieve an optimized image is minimized. The ability to begin every exam with consistent and repeatable settings can reduce the time to perform the exam. Imaging performance can also potentially be improved, since imaging parameter values that are found to work well are saved for use in subsequent exams.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An ultrasound imaging system comprising:
   image generating means for generating an ultrasound image in accordance with preselected imaging parameters;
   means for selecting a plurality of imaging parameter values to form a set of imaging parameter values;
   means for storing said set of imaging parameter values selected by a user while said image generating means is generating a desired ultrasound image, including means for storing a preset mode value representative of said set of imaging parameter values said set of imaging parameter values defining a preset mode; and
   means responsive to subsequent user selection of said preset mode value for automatically controlling said storage means to access said set of imaging parameter values to control image generating means in response to said stored set of imaging parameter values.

2. An ultrasound imaging system as defined in claim 1 further comprising means for selecting said set of imaging parameter values including a touch panel for parameter display and selection.

3. An ultrasound imaging system as defined in claim 2 wherein said means for selecting said set of imaging parameter values further includes one or more soft control devices for adjusting the values of said imaging parameters.

4. An ultrasound imaging system as defined in claim 2 wherein said means for automatically controlling said image generating means includes means for supplying said stored set of imaging parameter values to said touch panel in response to user selection of said preset mode.

5. An ultrasound imaging system as defined in claim 1 wherein said means for storing includes means for storing a plurality of sets of imaging parameter values, each set corresponding to a mode value, and wherein said means for automatically controlling said image generating means includes means responsive to user selection of a preset mode value for operating with the corresponding set of imaging parameter values.

6. An ultrasound imaging system as defined in claim 1 wherein said means for storing includes means for creating a new preset mode value from a currently active preset mode value.

7. An ultrasound imaging system as defined in claim 1 wherein said means for storing includes means for modifying a currently active user preset mode value.

8. An ultrasound imaging system as defined in claim 1 wherein said means for storing includes means for assigning a name to said preset mode value.

9. An ultrasound imaging system as defined in claim 1 wherein said preset mode value comprises an imaging mode value.

10. A method for operating an ultrasound imaging system which includes image generating means for generating an ultrasound image in accordance with preselected imaging parameters, said method comprising the steps of
    selecting a plurality of imaging parameter values to form a set of imaging parameter values:
    storing said set of imaging parameter values selected by a user while said image generating means is generating a desired ultrasound image, including storing a preset mode value representative of said set of imaging parameter values said set of imaging parameter values defining a preset mode; and
    automatically controlling said storing to access said set of imaging parameter values to control said image generating means in response to said stored set of imaging parameter values when a user selects said preset mode value.

11. A method as defined in claim 10 further including the steps of providing a touch panel for imaging parameter display and selection, and providing control devices for imaging parameter value adjustment.

12. A method as defined in claim 11 wherein the step of automatically controlling said image generating means includes supplying said stored set of imaging parameter values to said touch panel in response to user selection of said preset mode value.

13. A method as defined in claim 10 wherein the step of storing includes storing a plurality of sets of imaging parameter values, each set corresponding to a preset mode value, and wherein the step of controlling said image generating means includes responding to user selection of a preset mode value by operating with the corresponding set of imaging parameter values.

14. A method as defined in claim 13 wherein the step of storing a plurality of sets of imaging parameter values includes assigning a name to each of said plurality of preset mode value.

15. A method as defined in claim 10 wherein the step of storing a set of imaging parameter values includes creating a new preset mode value from a currently active preset mode value.

16. A method as defined in claim 10 wherein the step of storing a set of imaging parameter values includes modifying a currently active user preset mode value and storing the modified set of imaging parameter values.

17. A method as defined in claim 10 wherein the step of storing includes assigning a name to said preset mode value.

18. An ultrasound imaging system comprising:
    a scanner for ultrasound scanning of a desired region of a patient's body and for generating a scanner signal representative of ultrasound energy reflected from the desired region;

an image generator responsive to the scanner signal for generating an ultrasound image of the desired region in accordance with preselected imaging parameters;

means for selecting a plurality of imaging parameter values to form a set of imaging parameter values;

said touch panel for selection of a set of imaging parameter values while said image generator is generating a desired ultrasound image, including means for storing a preset mode value representative of said set of imaging parameter values said set of imaging parameter values defining a preset mode; and a control unit for controlling said scanner and said image generator during scanning and generation of an ultrasound image, said control unit including a memory for storing said set of imaging parameter values, and a processor responsive to subsequent user selection of said preset mode value for automatically controlling said storage means to access said set of imaging parameter values to control said scanner and said image generator in response to said stored set of imaging parameter values.

* * * * *